US012672979B2

(12) United States Patent
Coy et al.

(10) Patent No.: US 12,672,979 B2
(45) Date of Patent: Jul. 7, 2026

(54) COMBINED PESSARY AND MENSTRUAL CUP

(71) Applicant: The University of Toledo, Toledo, OH (US)

(72) Inventors: Lauren Coy, Toledo, OH (US); Joelle Gallais, Toledo, OH (US); Morgan Folley, Toledo, OH (US); Tara Dobric, Toledo, OH (US)

(73) Assignee: The University of Toledo, Toledo, OH (US)

( * ) Notice: Subject to any disclaimer, the term of this patent is extended or adjusted under 35 U.S.C. 154(b) by 428 days.

(21) Appl. No.: 18/234,006

(22) Filed: Aug. 15, 2023

(65) Prior Publication Data

US 2025/0057685 A1      Feb. 20, 2025

(51) Int. Cl.
A61F 6/08          (2006.01)
A61F 5/455          (2006.01)

(52) U.S. Cl.
CPC .............. A61F 5/4553 (2013.01); A61F 6/08 (2013.01); A61F 5/455 (2013.01)

(58) Field of Classification Search
CPC ...... A61F 5/4553; A61F 5/455; A61F 5/4404; A61F 6/08
See application file for complete search history.

(56) References Cited

U.S. PATENT DOCUMENTS

| | | | | |
|---|---|---|---|---|
| 2,534,900 | A * | 12/1950 | Chalmers | A61F 5/4553 |
| | | | | 604/330 |
| 3,371,664 | A * | 3/1968 | Pleshette | A61F 6/08 |
| | | | | 128/837 |

| | | | | |
|---|---|---|---|---|
| 4,703,752 | A * | 11/1987 | Gabbay | A61F 6/08 |
| | | | | 128/841 |
| 4,848,363 | A * | 7/1989 | Cattanach | A61F 5/4553 |
| | | | | 128/834 |
| 4,895,170 | A * | 1/1990 | Tlapek | A61F 6/08 |
| | | | | 128/832 |
| 5,771,900 | A * | 6/1998 | Austin | A61F 6/08 |
| | | | | 128/830 |
| 6,264,638 | B1 * | 7/2001 | Contente | A61M 31/002 |
| | | | | 604/285 |
| 6,796,973 | B1 * | 9/2004 | Contente | A61F 5/4553 |
| | | | | 128/832 |
| 10,016,308 | B2 * | 7/2018 | Knox | A61F 13/00085 |
| D864,390 | S * | 10/2019 | Sedic | D24/141 |
| D894,386 | S * | 8/2020 | LeClerc | D24/141 |

(Continued)

FOREIGN PATENT DOCUMENTS

| | | |
|---|---|---|
| CN | 108135732 B | 8/2020 |
| CN | 111246824 B | 3/2022 |

(Continued)

OTHER PUBLICATIONS

Keller, "Are Menstrual Cups Safe to Use With a Prolapse?", Dr. Lauren Keller Blog, Retrieved from Internet Aug. 22, 2023, URL, https://drlaurenkeller.com/blog/2020/7/29/are-menstrual-cups-safe-to-use-with-a-prolapse.

(Continued)

*Primary Examiner* — Guy K Townsend
(74) *Attorney, Agent, or Firm* — MacMillan, Sobanski & Todd, LLC

(57)          ABSTRACT

A combined pessary and menstrual cup useful for a human needing a pessary during menstruation is described.

20 Claims, 7 Drawing Sheets

(56)                References Cited

U.S. PATENT DOCUMENTS

| | | | | |
|---|---|---|---|---|
| D895,798 S | * | 9/2020 | Newman | D24/141 |
| D895,799 S | * | 9/2020 | Newman | D24/141 |
| D923,785 S | * | 6/2021 | Tsai | D24/141 |
| 11,219,548 B2 | | 1/2022 | Conti | |
| 11,583,433 B2 | | 2/2023 | Brush et al. | |
| 2007/0289598 A1 | * | 12/2007 | LaBarre | A61F 6/08 |
| | | | | 128/837 |
| 2008/0077097 A1 | * | 3/2008 | Chambers | A61F 5/4553 |
| | | | | 604/330 |
| 2008/0200888 A1 | * | 8/2008 | Gooch | A61F 5/4553 |
| | | | | 604/330 |
| 2016/0278988 A1 | * | 9/2016 | Knox | A61F 15/005 |
| 2018/0028350 A1 | * | 2/2018 | Wilson | A61F 5/4553 |
| 2019/0282350 A1 | * | 9/2019 | Conti | A61F 2/005 |
| 2019/0314191 A1 | * | 10/2019 | Bobarikin | A61F 5/4553 |
| 2019/0336318 A1 | * | 11/2019 | Kubo | A61F 5/4553 |
| 2020/0046572 A1 | * | 2/2020 | Hwang | A61F 5/4404 |
| 2020/0078208 A1 | * | 3/2020 | Stoebe-Latham | A61F 5/4553 |
| 2020/0078209 A1 | * | 3/2020 | Stoebe-Latham | |
| | | | | A61F 13/55105 |
| 2020/0179157 A1 | * | 6/2020 | Pitacco | A61F 5/44 |
| 2020/0214617 A1 | * | 7/2020 | Sham | G16H 40/63 |
| 2020/0214876 A1 | * | 7/2020 | Tsai | A61F 5/4553 |
| 2021/0113363 A1 | * | 4/2021 | Evans | A61F 5/4553 |
| 2025/0057685 A1 | * | 2/2025 | Coy | A61F 6/08 |

FOREIGN PATENT DOCUMENTS

| | | | |
|---|---|---|---|
| EP | 2567680 B1 | 3/2016 | |
| WO | 2015041353 A1 | 3/2015 | |
| WO | 2021069619 A1 | 4/2021 | |

OTHER PUBLICATIONS

Amazon, Intimina Ziggy Cup 2-Extra-Thin Reusable Menstrual Disc, Period Cup, Disposable Menstrual Cup, with Flat-fit Design, Period Disc, Menstrual Cups Ring, Period Products (Size B), Retrieved from Internet Aug. 22, 2023, URL, https://www.amazon.com/Intimina-Ziggy-Cup-Generation-Ultra-Thin/dp/B09Q3MKXVD?th=1.

* cited by examiner

100

100

COMBINED PESSARY AND MENSTRUAL CUP

RELATED APPLICATIONS

None.

STATEMENT REGARDING FEDERALLY SPONSORED RESEARCH

This invention was made with no government support. The government has no rights in this invention.

BACKGROUND

There are challenges for people who menstruate when utilizing a pessary. For example, using a pad in conjunction with a pessary is not comfortable for many people. Furthermore, blood will often stain a pessary. Therefore, some people who use pessaries own a second pessary for use while menstruating. There is a need in the art for new and improved alternatives to using a pad while also needing the functions of a pessary to support pelvic organs.

SUMMARY

Provided herein is a combined pessary and menstrual cup comprising a ring portion comprising a knob extending outwardly from a base ring; and a cup portion extending from the base ring to a cup bottom point and defining an internal volume configured to retain a volume of liquid, wherein the base ring defines an opening to the internal volume.

In certain embodiments, the internal volume is in a range of from about 8 mL to about 79 mL.

In certain embodiments, the knob takes up from about one-eighth to about one-fourth of a circumference of the base ring.

In certain embodiments, the knob has a thickness diameter measured from a top surface of the knob to a bottom surface of the knob, the base ring has a thickness diameter measured from a top surface of the base ring to a bottom surface of the base ring, and the thickness diameter of the knob is larger than the thickness diameter of the base ring. In particular embodiments, the thickness diameter of the knob is from about 10% larger to about 300% larger than the thickness diameter of the base ring. In particular embodiments, the thickness diameter of the knob is about two times larger than the thickness diameter of the base ring.

In certain embodiments, the knob is trapezoidal in shape.

In certain embodiments, the knob is solid. In certain embodiments, the knob is hollow.

In certain embodiments, the combined pessary and menstrual cup further comprises a support member spanning the opening. In particular embodiments, the support member comprises at least one hole therethrough.

In certain embodiments, the cup portion extends from an exterior surface of the base ring, and wherein the cup bottom point is concentric with the base ring.

In certain embodiments, the cup portion extends from an interior surface of the base ring, and wherein the cup bottom point is concentric with the base ring.

In certain embodiments, the cup portion extends from a bottom surface of the base ring, and wherein the cup bottom point is concentric with the base ring.

In certain embodiments, the combined pessary and menstrual cup further comprises a stem protruding from the cup portion. In particular embodiments, the stem extends from the cup bottom portion to the knob. In particular embodiments, the stem protrudes from the knob.

Further provided herein is a combined pessary and menstrual cup comprising a ring portion comprising a base ring; and a cup portion extending from an interior surface of the base ring to a cup bottom point and defining an internal volume configured to retain a volume of liquid, wherein the base ring defines an opening to the internal volume; wherein the base ring has a thickness diameter measured from a top surface of the base ring to a bottom surface of the base ring, the cup portion has a cup height measured from a plane defined by a bottom surface of the base ring to a parallel plane defined by the cup bottom point, and a ratio of the thickness diameter to the cup height is from about 0.60:1 to about 3:1. In certain embodiments, the thickness diameter is greater than 75% of the cup height.

In certain embodiments, the combined pessary and menstrual cup has a height measured from a plane defined by a top surface of the base ring to a parallel plane defined by the cup bottom point, and the thickness diameter is at least half of the height.

In certain embodiments, the combined pessary and menstrual cup further comprises a stem extending from the cup bottom point.

DETAILED DESCRIPTION

Figure 1:
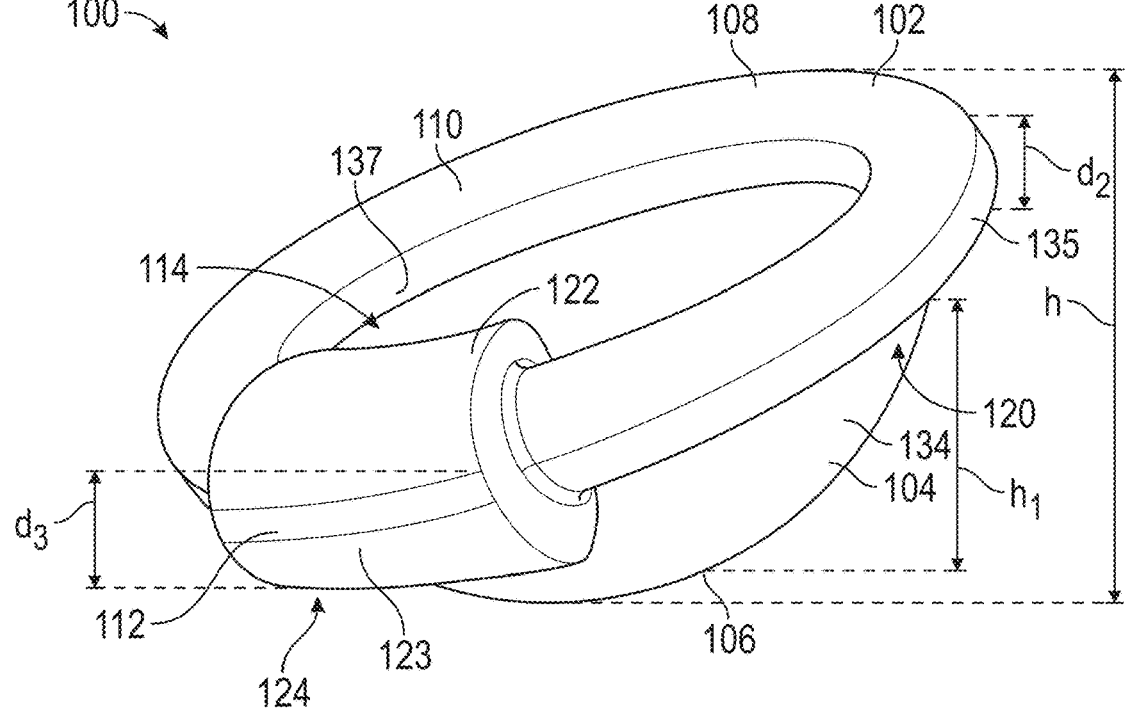
FIG. 1: Perspective view of a first non-limiting example embodiment of a combined pessary and menstrual cup.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

A pessary is a device inserted into a vagina to provide support to the vaginal tissues displaced by pelvic organ prolapse. There are many different forms of pelvic organ prolapse, and therefore there are many different shapes and configurations of pessaries. A menstrual cup or disc is a fluid-retaining device inserted into a vagina to collect blood from menstruation. Menstrual cups or discs are alternatives to pads and tampons. In accordance with the present disclosure, the functionalities of a pessary and a menstrual cup or disc may be combined in a single device. The combined pessary and menstrual cup may have many different shapes, sizes, and configurations based on the particular condition the pessary functionality is intended to address. The combined pessary and menstrual cup is useful for any human (including, but not limited to, ciswomen, non-binary people, agender people, transgender men, etc.) needing a pessary during menstruation.

Provided herein are two non-limiting example embodiments of a combined pessary and menstrual cup device configured to combine the functionalities of a pessary with a menstrual cup or disc and provide menstrual cycle support for menstruating people suffering from pelvic organ prolapse and/or urinary incontinence. Each of FIGS. 1-5 illustrates a perspective view of a first example embodiment of the combined pessary and menstrual cup 100 useful for treating urinary incontinence. Referring now to FIGS. 1-5, the combined pessary and menstrual cup 100 includes a ring portion 102 and a cup portion 104. The illustrated combined pessary and menstrual cup 100 has a height h that is approximately 35 mm (1.37795 in), measured from a plane defined by a cup bottom point 106 to a parallel plane defined by a ring top surface 108. However, although a height h of 35 mm (1.37795 in) is described for example purposes, the combined pessary and menstrual cup 100 can have any height h so long as the combined pessary and menstrual cup 100 fits within the vaginal canal of the user. In some examples, the height h can range from about 15 mm (0.590551 in) to about 120 mm (4.72441 in).

Referring still to FIGS. 1-5, the combined pessary and menstrual cup 100 includes a ring portion 102 having a base ring 110, a knob 112, and an opening 114. The combined pessary and menstrual cup 100 can be made from medical grade silicone. However, other materials are possible and encompassed within the scope of the present disclosure. The circular shape of the base ring 110 forms a continuous loop. In some examples, the continuous loop has a loop diameter $d_1$ of 85 mm (3.34646 in), measured from a first side 116 to a second side 118 of the ring portion 102. However, the continuous loop can have any loop diameter $d_1$ suitable to provide the functionality of a pessary. In some embodiments, the loop diameter $d_1$ may be from about 51 mm (2.00787 in) to about 102 mm (4.01575 in). However, the combined pessary and menstrual cup 100 is not limited to this range of loop diameters $d_1$. In one non-limiting example, the loop diameter $d_1$ is approximately 85 mm (3.34646 in). In use, the loop diameter $d_1$ being about 85 mm (3.34646 in) allows for the ring portion 102 to provide adequate relief from urinary incontinence because it causes the knob 112 to apply sufficient pressure to the urethra to prevent urine from escaping during movement.

Figure 4:
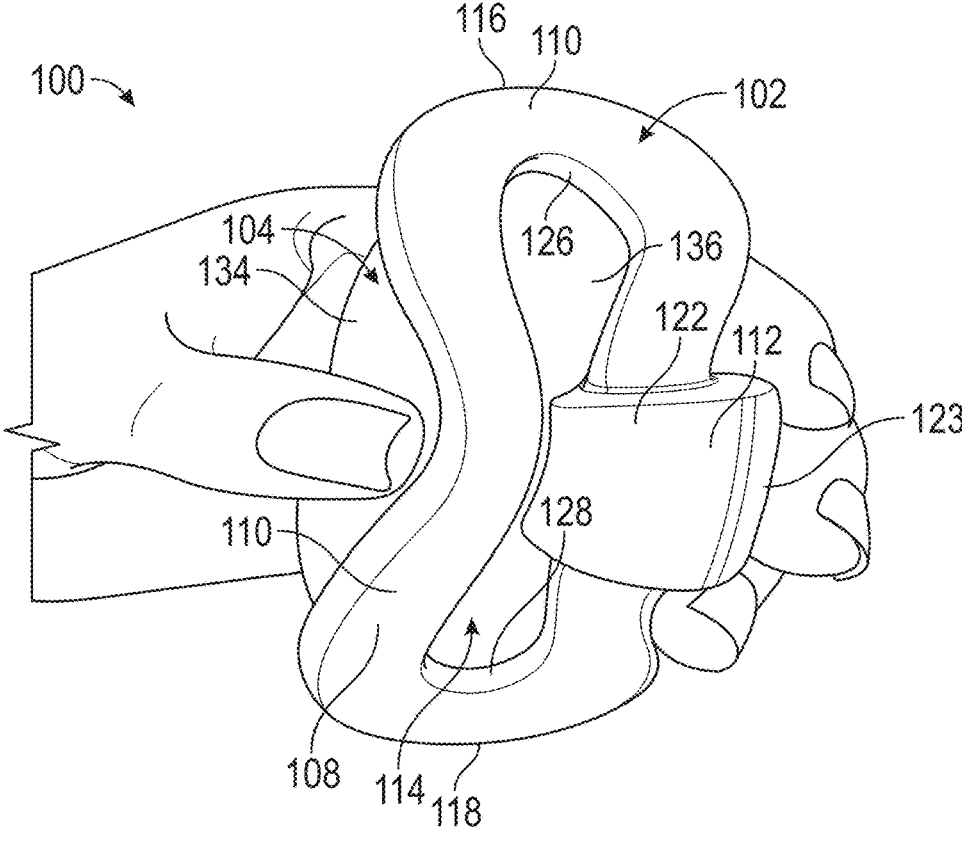
FIG. 4: View of the first non-limiting example embodiment of the combined pessary and menstrual cup being deformed.

Referring still to FIGS. 1-5, the base ring 110 can have a thickness diameter $d_2$ of approximately 10 mm (0.393701 in), measured from the top surface 108 of the base ring 110 to a bottom surface 120 of the base ring 110. However, the thickness diameter $d_2$ can be any suitable size. For example, the thickness diameter $d_2$ can be from about 5 mm (0.19685 in) to about 40 mm (1.5748 in). Also, the base ring 110 can be solid, hollow, or semi hollow, so long as the base ring 110 is flexible enough for insertion into, and removal from, a vagina. The flexibility of the combined pessary and menstrual cup 100 can be best seen in each of FIGS. 3 and 4, where the combined pessary and menstrual cup 100 is depicted as deformed. In FIG. 4, a user's hand is shown applying pressure to deform the combined pessary and menstrual cup 100 in preparation for insertion into a vagina.

Referring still to FIGS. 1-5, the ring portion 102 includes the knob 112 which is located on, or integral with, a portion of the base ring 110. The knob 112 protrudes from, or extends outwardly from, the base ring 110. It does not matter where on the base ring 110 the knob 112 is located so long as the knob 112 protrudes or extends outwardly relative to the base ring 110. The knob 112 as illustrated in FIGS. 1-5 extends outwardly in all directions. However, in certain embodiments, the knob 112 only extends outwardly from the base ring 110 opposite the opening 114 and does not extend into the opening 114, to apply pressure to a target organ. As noted above, the knob 112 extending outwardly from the base ring 110 causes pressure to be applied the urethra of the person using the combined pessary and menstrual cup 100. The knob 112 can take up anywhere from about one-eighth to about one-fourth of the circumference of the base ring 110, where the circumference of the base ring is measured as if the knob 112 were not present (i.e., the circumference of the base ring 110 runs through the knob 112). However, the proportion of the circumference of the base ring 110 that is taken up by the knob 112 can vary.

Referring still to FIGS. 1-5, the knob 112 further has a thickness diameter $d_3$ measured from a top surface 122 of the knob 112 to a bottom surface 124 of the knob 112, where the thickness diameter da is larger than the thickness diameter $d_2$ of the base ring 110. In particular, the thickness diameter $d_3$ of the knob 112 may be from about 10% larger to about 300% larger than the thickness diameter $d_2$ of the base ring 110. In the non-limiting example depicted in FIGS. 1-5, the thickness diameter $d_3$ of the knob 112 is approximately two times the size of the thickness diameter $d_2$ of the base ring 110. In other words, the thickness diameter $d_3$ of the knob 112 is approximately 20 mm (0.787402 in). However, other thickness diameters $d_3$ are possible and encompassed within the scope of the present disclosure. In some examples, the thickness diameter $d_3$ ranges from about 10 mm (0.393701 in) to 50 mm (1.9685 in). The thickness diameter $d_3$ of the knob 112 being about 20 mm (0.787402 in) has been found to be advantageous at least because this diameter allows for a sufficient amount of pressure to be applied against the urethra of a user experiencing urinary incontinence.

As seen in FIGS. 1-5, the knob 112 can be trapezoidal in shape. However, the knob 112 does not need to be trapezoidal. The knob 112 can be shaped in any desired manner including, but not limited to, semicircular, rectangular, octagonal, or nonagonal. The shape of the knob 112 being trapezoidal is beneficial at least because a trapezoidal shaped knob 112 provides a larger surface area on one side 123 than the other. The side 123 with the largest surface area extends outwardly from the opening 114 of the base ring 110. This allows the knob 112 to apply pressure to the urethra as mentioned above, thereby helping to prevent urination from coughing sneezing, laughing, or exercising. Furthermore, the knob 112 can be solid or hollow. However, it is advantageous for the knob 112 to be solid at least because having a solid knob 112 allows for minimal flexion of the knob 112, which in turn permits adequate pressure to be applied to the target vaginal tissues or other anatomical location.

Figure 5:
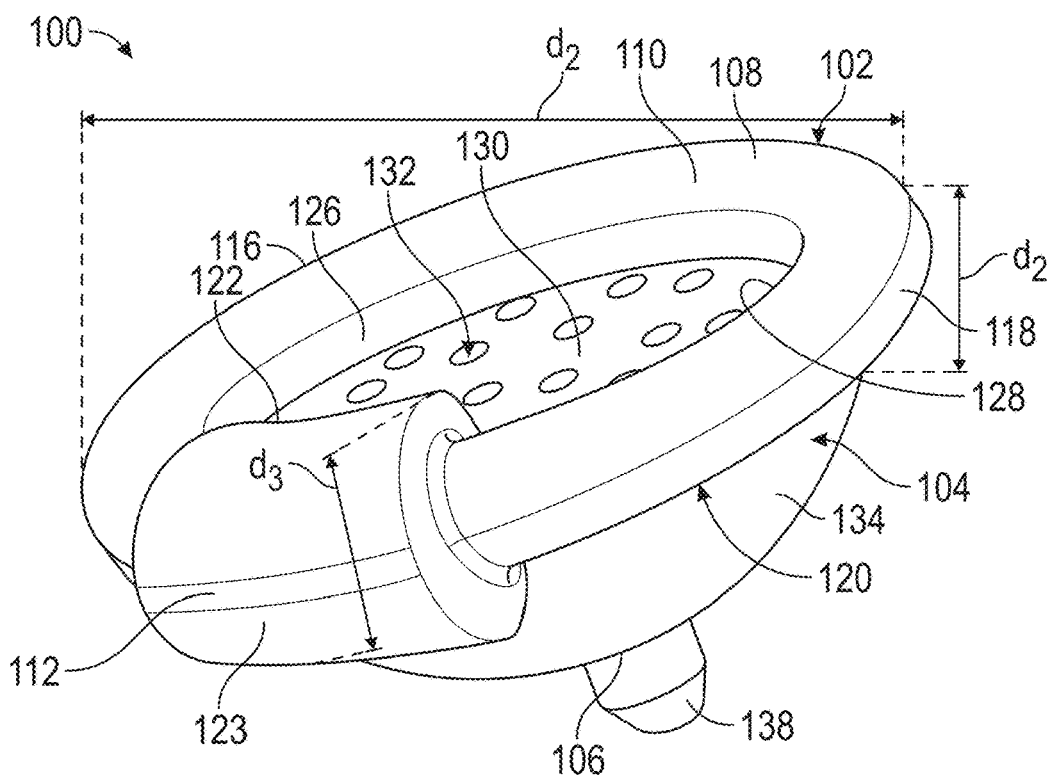
FIG. 5: Illustration of the first non-limiting example embodiment of the combined pessary and menstrual cup having a stem.

Referring still to FIGS. 1-5, the opening 114 is configured to provide access of fluids into the cup portion 104. The opening 114 of the ring portion 102 can be any size desired so long as the opening 114 is of a size that allows for the discharge of blood and mucosal tissue from the inner lining of a uterus to enter the cup portion 104. The opening 114 can have an opening diameter $d_4$ that is approximately 65 mm (2.55906 in). However, the opening diameter $d_4$ can be from about 10 mm (0.393701 in) to about 95 mm (3.74016 in). The opening diameter $d_4$ is measured from a third side 126 to a fourth side 128 of the base ring 110. The opening diameter $d_4$ being 65 mm (2.55906 in) is advantageous for providing ideal flexibility of the ring portion 102 as well as good retention of blood in the cup portion 104. Alternatively, as shown in FIG. 5, the opening 114 can be filled with a support member 130 having at least one hole 132 therethrough. The support member 130 spans the opening 114. The support member 130 provides additional support to the ring portion 102 to make the ring portion 102 slightly less flexible, thus allowing for additional support to be applied to a targeted organ, while still allowing blood to travel into and be retained by the cup portion 104.

Referring still to FIGS. 1-5, the cup portion 104 extends from a bottom surface 120 of the base ring 110, in a direction away from the base ring 110 to converge at a bottom point 106 concentric with, but displaced relative to, the base ring 110 so as to define an internal volume and form a receptacle capable of retaining a liquid. For clarity, the term "bottom point" does not imply any particular shape, but, rather, refers to the bottom-most location of the cup portion 104 relative to the base ring 110. The bottom point 106 may be simply a location on a rounded surface, as shown in FIG. 1, or may alternatively be a pointed apex. The opening 114 provides access to the internal volume of the cup portion 104. However, although the illustrated embodiment shows the cup portion 104 extending from the bottom surface 120 of the base ring 110, the cup portion 104 can alternatively or in addition extend from the exterior side 135 of the base ring 110 or from the interior side 137 of the base ring 110. It is advantageous for the cup portion 104 to extend from the bottom surface 120 of the base ring 110 at least because it allows for easier cleaning of the combined pessary and menstrual cup 100. In embodiments where the cup portion 104 extends from the exterior side 135 of the base ring 110, blood or mucus may become trapped in a crevice that is difficult to clean. However, despite this, there are also benefits to having the cup portion 104 extend from the exterior side 135. Specifically, this can allow for a larger amount of liquid to be contained without needing to make the height h of the combined pessary and menstrual cup 100 any larger. It is also advantageous for the cup portion 104 to extend from the interior side 137 because this allows for better a better seal to be formed against a vaginal canal wall when the combined pessary and menstrual cup 100 is inserted.

Referring still to FIGS. 1-5, the cup portion 104 can have cup height $h_1$ of about 25 mm (0.984252 in). However, the cup height h) can be any desired height so long as the combined pessary and menstrual cup 100 fits within the vaginal canal and the internal volume of the cup portion 104 is adequate to capture and retain a desired amount of liquid. For example, the cup height $h_1$ can range from about 10 mm (0.393701 in) to about 80 mm (3.14961 in). The cup height $h_1$ is measured from a plane defined by the bottom surface 120 of the base ring 110 to a parallel plane defined by the cup bottom point 106. The cup height $h_1$ is also equal to the distance from a center point of the diameter $d_4$ to the cup bottom point 106. Put another way, the cup height $h_1$ is equal to the height of the cup portion 104 at its tallest point in the center of the opening 114.

Figure 2:
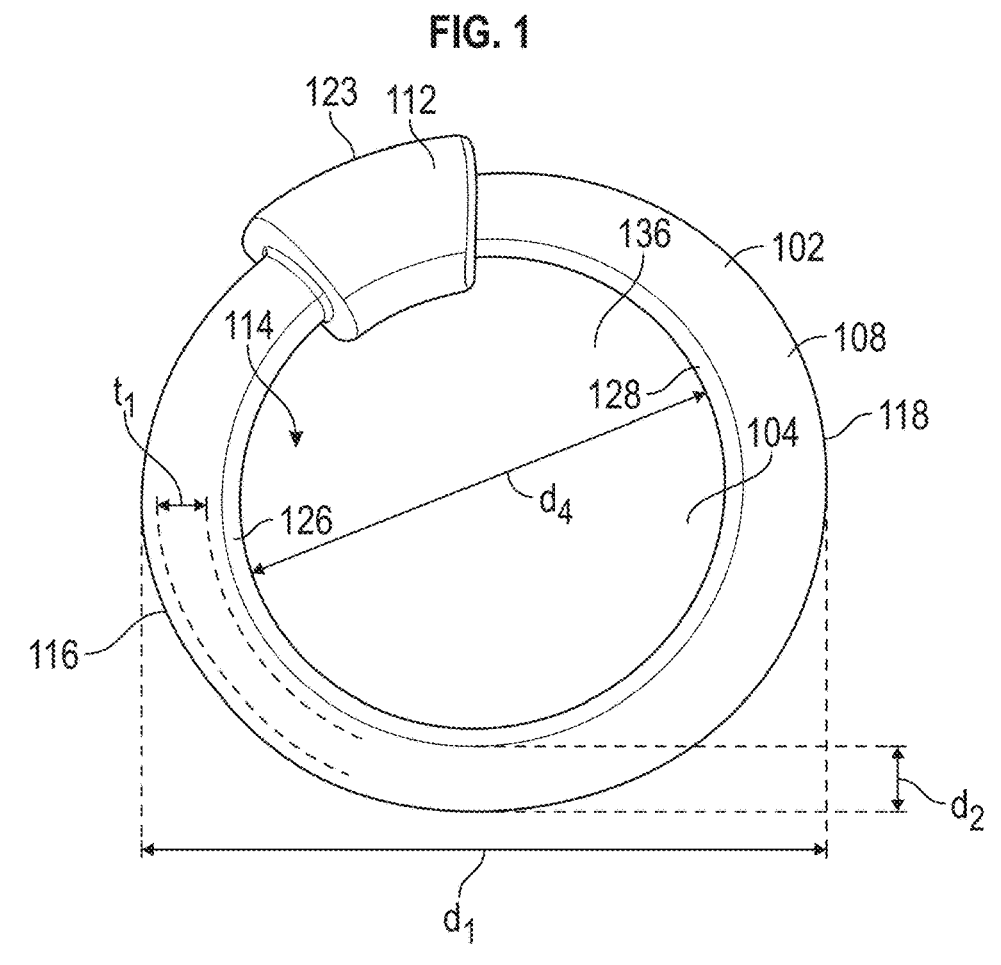
FIG. 2: Top view of a first non-limiting example embodiment of a combined pessary and menstrual cup.
Figure 3:
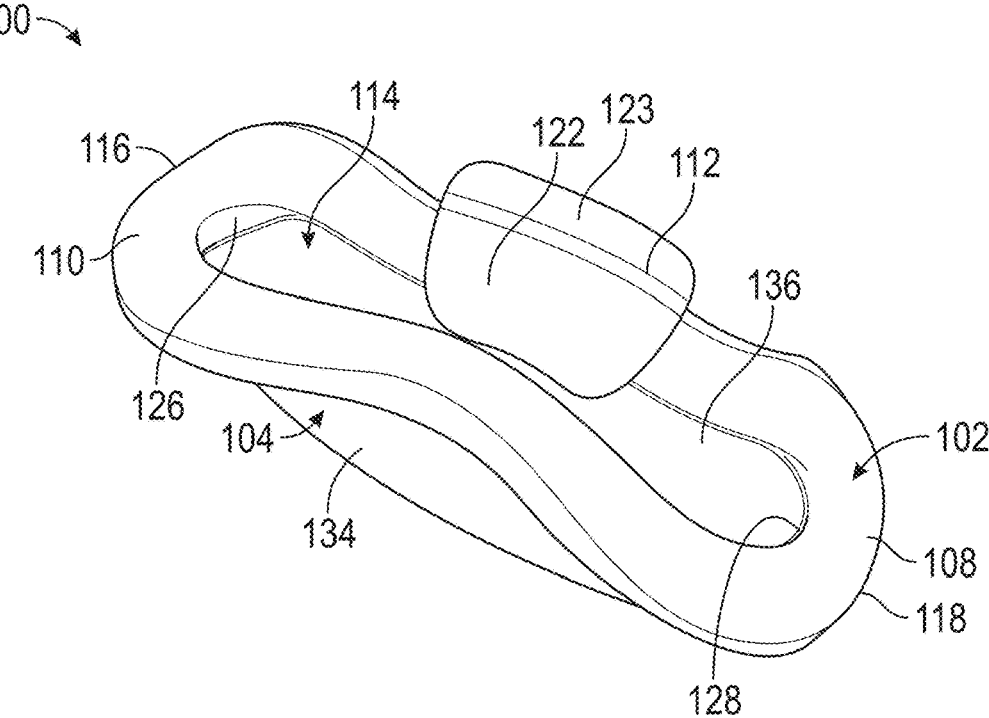
FIG. 3: View of the first non-limiting example embodiment of the combined pessary and menstrual cup being deformed.

Referring to FIGS. 1-2, the cup portion 104 can have a cup thickness $t_1$ of approximately 5 mm (0.19685 in). The cup thickness $t_1$ is measured from a cup exterior surface 134 to a cup interior surface 136. However, the cup portion 104 can have any desired cup thickness $t_1$ that still permits the combined pessary and menstrual cup 100 to be flexible enough for insertion and removal from the intended anatomical location. For example, the cup thickness $t_1$ can range from about 2 mm (0.0787402 in) to about 10 mm (0.393701 in). This range provides for ideal flexibility and comfort, as smaller sizes may tear more easily and may be uncomfortable for a user. Depending on the precise dimensions, the cup portion 104 can hold from about 8 mL to about 79 mL of liquid.

Referring now to FIG. 5, optionally, the combined pessary and menstrual cup 100 may have a stem 138 that can be used to help remove the combined pessary and menstrual cup 100 from a vaginal canal. The stem 138 can be any size or shape desired, so long as a user can easily utilize the stem 138 to remove the combined pessary and menstrual cup 100 from the vaginal canal. Although any desired shape or size is appropriate, the stem 138 may be formed from a piece of silicone ranging from approximately 10 mm (0.393701 in) to approximately 20 mm (0.787402 in). This range allows the user of the combined pessary and menstrual cup 100 to easily grip the stem 138 for removal of the combined pessary and menstrual cup 100 while also not being so large as to cause discomfort when the combined pessary and menstrual cup 100 is in place within the body. However, the stem 138 may be larger, and such larger sizes are encompassed within the scope of the present disclosure. For example, a stem 138 of up to about 47 mm (1.85039 in) in length can be beneficial in some circumstances, such as when a user of the combined pessary and menstrual cup 100 has a disability that prevents easy gripping of the stem 138, in which case a larger stem 138 may be preferred. Furthermore, the stem 138 can be any shape including, but not limited to, triangular, circular, or rectangular. A circular shaped stem 138 with a hole therethrough is particularly advantageous so that a user can easily grasp the stem 138 by putting a finger through the hole of the stem 138.

The stem 138 can be located at any point on the cup portion 104 or the ring portion 102. Having the stem 138 located on the cup bottom point 106 allows the stem 138 to be easily reached by a user. However, as another example, the stem 138 may be located on the knob 112, or may extend from the knob 112 towards the direction of the cup bottom point 106. This allows a user to more easily break the seal formed between the combined pessary and menstrual cup 100 and the vaginal canal, as the knob 112 can be the point where the most pressure against the vaginal canal occurs. Applying a pulling pressure in relation to the knob 112 causes the seal to break, allowing for easy removal of the combined pessary and menstrual cup 100. The stem 138 may alternatively be located elsewhere on the base ring 110 or even on the exterior surface 134 of the cup portion 104.

Figure 9:
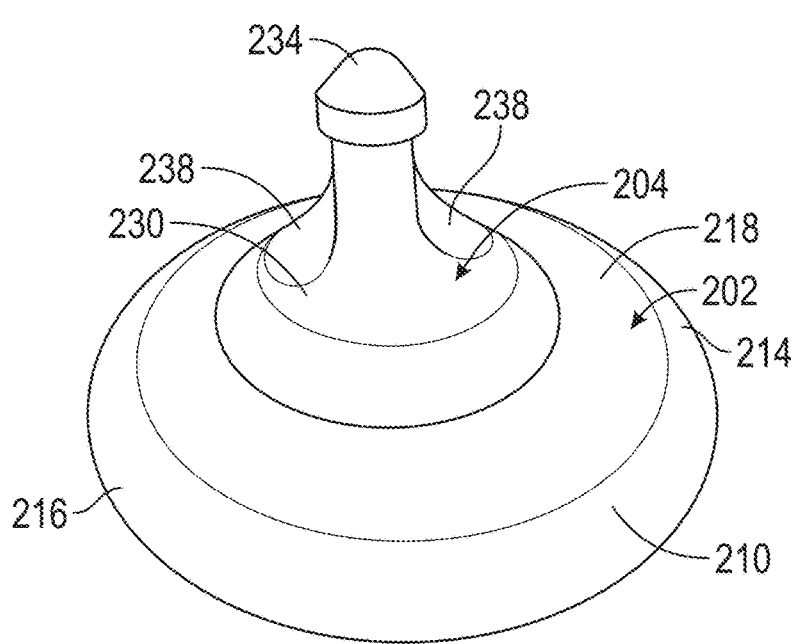
FIG. 9: Illustration of the second non-limiting example embodiment of the combined pessary and menstrual cup being deformed.
Figure 10:
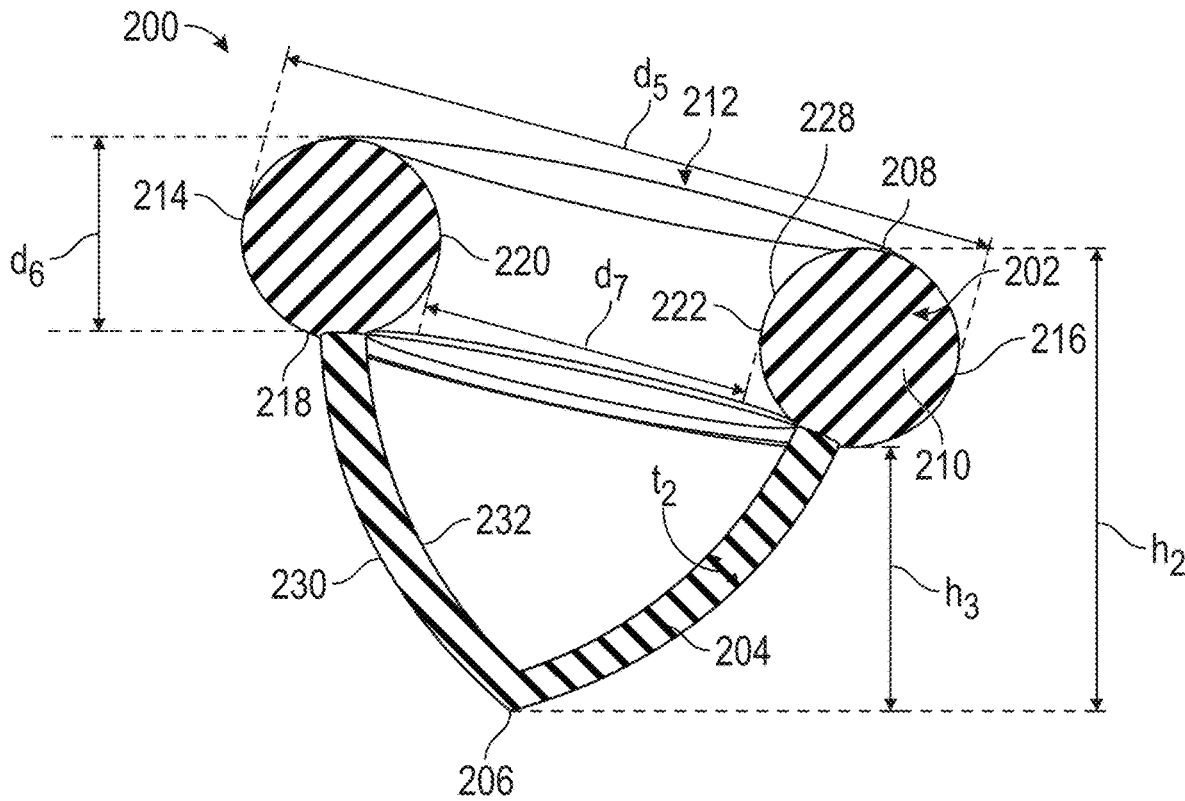
FIG. 10: Illustration of the second non-limiting example embodiment of the combined pessary and menstrual cup.

Each of FIGS. 6-11 illustrates a perspective view of a second example embodiment of the combined pessary and menstrual cup 200 useful for treating a pelvic organ prolapse. The combined pessary and menstrual cup 200 includes a ring portion 202 and a cup portion 204. The combined pessary and menstrual cup 200 has a height $h_2$ that is approximately 45 mm (1.77165 in), where the height $h_2$ is measured from a plane defined by a cup bottom point 206 to a parallel plane defined by the top surface 208 of a base ring 210. However, although a height $h_2$ of 45 mm is described for example purposes, the combined pessary and menstrual cup 200 can have other heights $h_2$ so long as the combined pessary and menstrual cup 200 fits within the vaginal canal. In some embodiments, the combined pessary and menstrual cup 200 has a height $h_2$ in the range of from about 15 mm (0.590551 in) to about 120 mm (4.72441 in). Furthermore, the term "bottom point" again does not imply any particular shape, but, rather, refers to the bottom-most location of the cup portion 204 relative to the base ring 210. The bottom point 206 may be simply a location on a rounded surface, or may alternatively be a pointed apex such as shown in FIG. 10.

Referring still to FIGS. 6-11, the ring portion 202 has a base ring 210 defining an opening 212. The combined pessary and menstrual cup 200 can be made from medical grade silicone. However, other materials are possible and encompassed within the scope of the present disclosure. The circular shape of the base ring 210 forms a continuous loop with a loop diameter $d_5$ of from about 51 mm (2.00787 in) to about 95 mm (3.74016 in), where the loop diameter $d_5$ is measured from a first side 214 of the base ring 210 to a second side 216 of the base ring 210. The loop diameter $d_5$ being from about 51 mm (2.00787 in) to about 95 mm (3.74016 in) allows for the ring portion 202 to better help users suffering from postpartum pelvic organ prolapse as it allows for the base ring 210 to apply pressure to the uterus or rectum. However, other loop diameters $d_5$ are possible and encompassed within the scope of the present disclosure. Furthermore, the base ring 210 has a thickness diameter $d_6$ of approximately 40 mm (1.5748 in), where the thickness diameter $d_6$ is measured from the top surface 208 of the base ring 210 to the bottom surface 218 of the base ring 210. However, the thickness diameter $d_6$ can be any desired diameter depending on the size and shape of a user's vagina or the specific type of prolapse being treated with the combined pessary and menstrual cup 200. For example, the thickness diameter $d_6$ of the base ring 210 can be from about 20 mm (0.787402 in) to about 60 mm (2.3622 in). The thickness diameter $d_6$ may account for anywhere from about 20% to about 70% of the height $h_2$. In some embodiments, the thickness diameter do is about 50% of the height $h_2$. Also, the base ring 210 can be solid, hollow, or semi hollow, so long as the base ring 210 is flexible enough for insertion into, and removal from, a vagina. A hollow base ring 210 or a semi-hollow base ring 210 is generally more flexible than a solid base ring 210, and therefore provides more flexibility for the combined pessary and menstrual cup 200.

Referring still to FIGS. 6-11, the opening 212 within the circumference of the base ring 210 is configured to allow a fluid to enter the cup portion 204. The opening 212 can be any desired size so long as the opening 212 allows for blood and mucosal tissue from the inner lining of a uterus to enter the cup portion 204. The opening 212 may have an opening diameter $d_7$ that is approximately 20 mm (0.787402 in). However, the opening diameter $d_7$ can range from about 10 mm (0.393701 in) to about 95 mm (3.74016 in). The opening diameter $d_7$ is measured from a third side 220 of the base ring 210 to a fourth side 222 of the base ring 210. Alternatively, the opening 212 can be replaced with the support member 130 spanning the opening 212, as shown in FIG. 5 in the context of the first embodiment of the combined pessary and menstrual cup 100, having the at least one hole 132 therethrough. The support member 130 provides additional support to the ring portion 202 making it slightly less flexible, thus allowing for additional support to be applied to a targeted organ or anatomical area.

Referring still to FIGS. 6-11, the cup portion 204 extends from a bottom surface 218 of the base ring 210 to converge at a bottom point 206 concentric with, but displaced relative to, the base ring 210 so as to form a receptacle capable of retaining a liquid. Although FIGS. 6-11 show that the cup portion 204 extends from the bottom surface 218 of the base ring 210, the cup portion 204 can alternatively extend from an exterior surface 226 of the base ring 210 or the interior surface 228 of the base ring 210. It is advantageous for the cup portion 204 to extend from the bottom surface 218 of the base ring 210 because it allows for easier cleaning of the combined pessary and menstrual cup 200. In embodiments where the cup portion 204 extends from the exterior surface 226 of the base ring 210, blood or mucus may become trapped in a crevice that is difficult to clean. However, such embodiments are nonetheless encompassed within the scope of the present disclosure. It is also advantageous for the cup portion 204 to extend from the interior surface 228 because this allows for a better seal to form when the combined pessary and menstrual cup 200 is positioned within a vaginal canal. Further, FIG. 9 illustrates two indentations 238 in the cup portion 204. The indentations 238 demonstrate the flexibility of the cup portion 204 when pressure is applied to the cup portion 204 such as with a user's fingers. The flexibility of the cup portion 204 allows for easier insertion of the combined pessary and menstrual cup 200.

Referring still to FIGS. 6-11, the cup portion 204 has a cup height ha of about 30 mm (1.1811 in). The cup height $h_3$ is measured from a plane defined by the bottom surface 218 of the base ring 210 to a parallel plane defined by the cup bottom point 206. The cup height $h_3$ is also equal to the distance from a center point of the diameter $d_7$ to the cup bottom point 206. Put another way, the cup height ha is equal to the height of the cup portion 204 at its tallest point in the center of the opening 212. However, the cup height ha can be any desired height so long as the combined pessary and menstrual cup 200 fits within the vaginal canal and the internal volume of the cup portion 204 is adequate to capture and retain a desired amount of liquid. For example, the cup height ha can range from about 10 mm (0.393701 in) to about 80 mm (3.14961 in). The combined pessary and menstrual cup 200 may have a ratio of thickness diameter do to cup height $h_3$ of from about 0.60:1 to about 3:1. In some embodiments, the combined pessary and menstrual cup 200 has a ratio of thickness diameter $d_6$ to cup height $h_3$ of about 1:1. In some embodiments, the thickness diameter do is greater than 75% of the cup height $h_3$.

Referring still to FIGS. 6-11, the cup portion 204 can have a cup thickness $t_2$ of approximately 5 mm (0.19685 in), measured from a cup exterior surface 230 to a cup interior surface 232. However, the cup portion 204 can have any desired cup thickness $t_2$. For example, the cup thickness $t_2$ can range from about 2 mm (0.0787402 in) to about 10 mm (0.393701 in). This range provides for sufficient flexibility and comfort. A smaller cup thickness $t_2$ may tear too easily, while a larger cup thickness $t_2$ may be uncomfortable for the user. The cup portion 204 defines an internal volume capable of retaining a liquid. In some embodiments, the cup portion 204 has an internal volume capable of holding a quantity of liquid in the range of from about 8 mL to about 79 mL (i.e., the cup portion 204 has an internal volume of from about 8 mL to about 79 mL).

Figure 6:
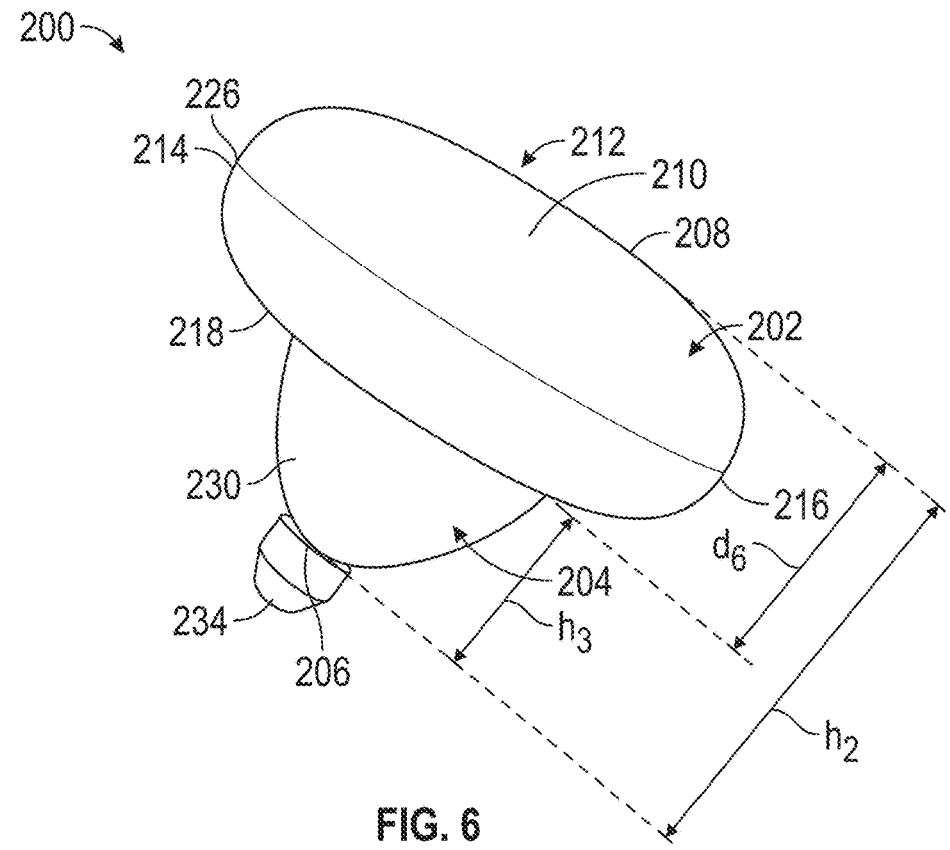
FIG. 6: Illustrations of a second non-limiting example embodiment of a combined pessary and menstrual cup.
Figures 7, 8:
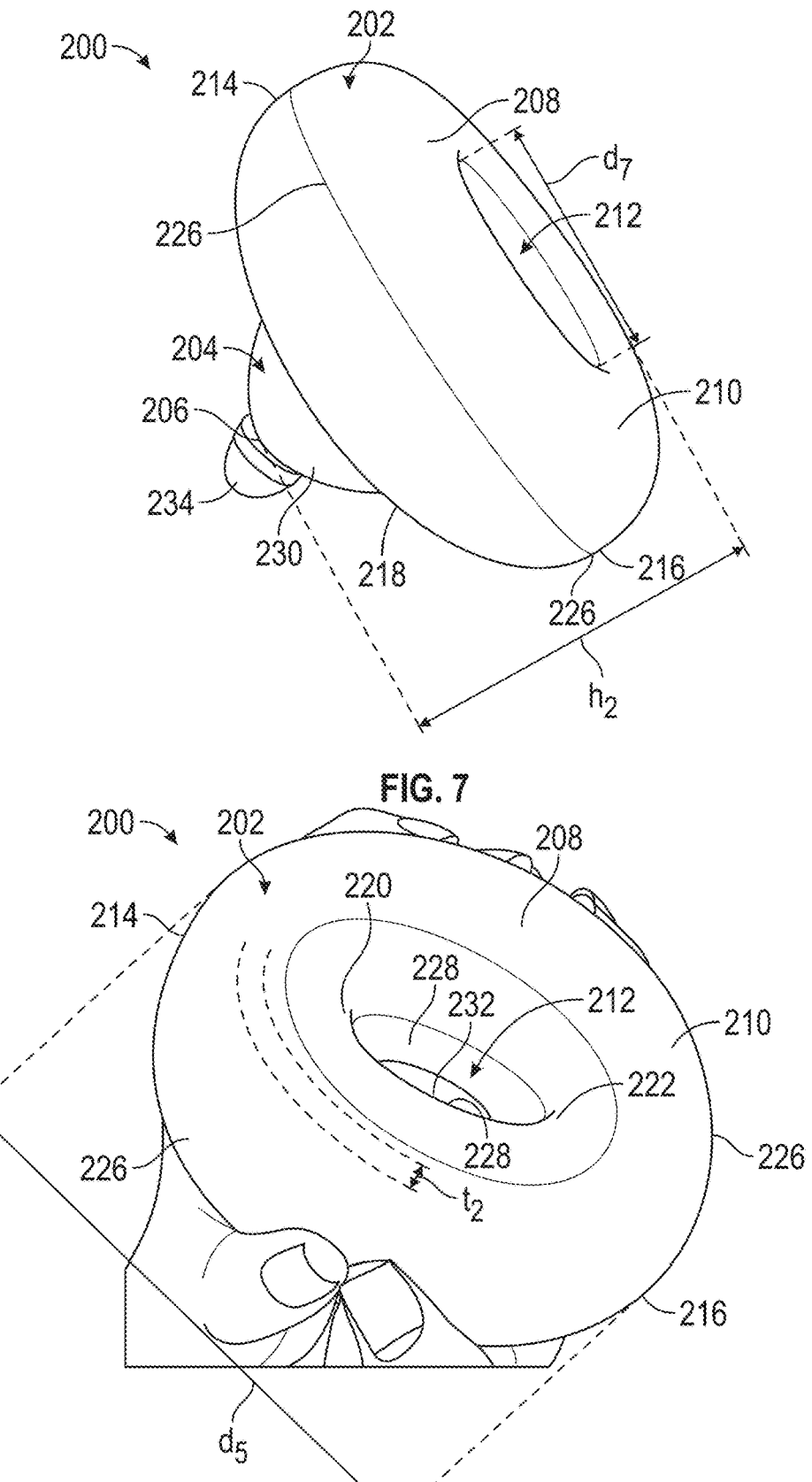
FIG. 7: Illustration of the second non-limiting example embodiment of the combined pessary and menstrual cup.
FIG. 8: Illustrations of the second non-limiting example embodiment of the combined pessary and menstrual cup being deformed.

Referring now to FIGS. 6, 7, and 9, optionally, the combined pessary and menstrual cup 200 may have a stem 234 that can be used to help remove the combined pessary and menstrual cup 200 from a vaginal canal. The stem 234 can be any size or shape desired, so long as the stem 234 allows a person to easily remove the combined pessary and menstrual cup 200 from a vaginal canal. Although any desired shape or size is appropriate, the stem 234 may be formed from a piece of silicone ranging from approximately 10 mm (0.393701 in) in length to approximately 20 mm (0.787407 in) in length, such that the stem 234 extends away from the cup bottom point 206 for a distance of from about 10 mm to about 20 mm. This range of sizes allows for the combined pessary and menstrual cup 200 to be easily gripped by the stem 234 for removal of the combined pessary and menstrual cup 200, while also not being so large as to cause discomfort while the combined pessary and menstrual cup 200 is in place within the body. However, larger or smaller stems 234 are possible and encompassed within the scope of the present disclosure. For example, stems 234 of up to 47 mm (1.85039 in) in length can be beneficial in some circumstances, such as where a user has a disability preventing them from gripping a smaller stem 234. Furthermore, the stem 234 can be any shape including, but not limited to, triangular, circular, or rectangular.

Figure 11:
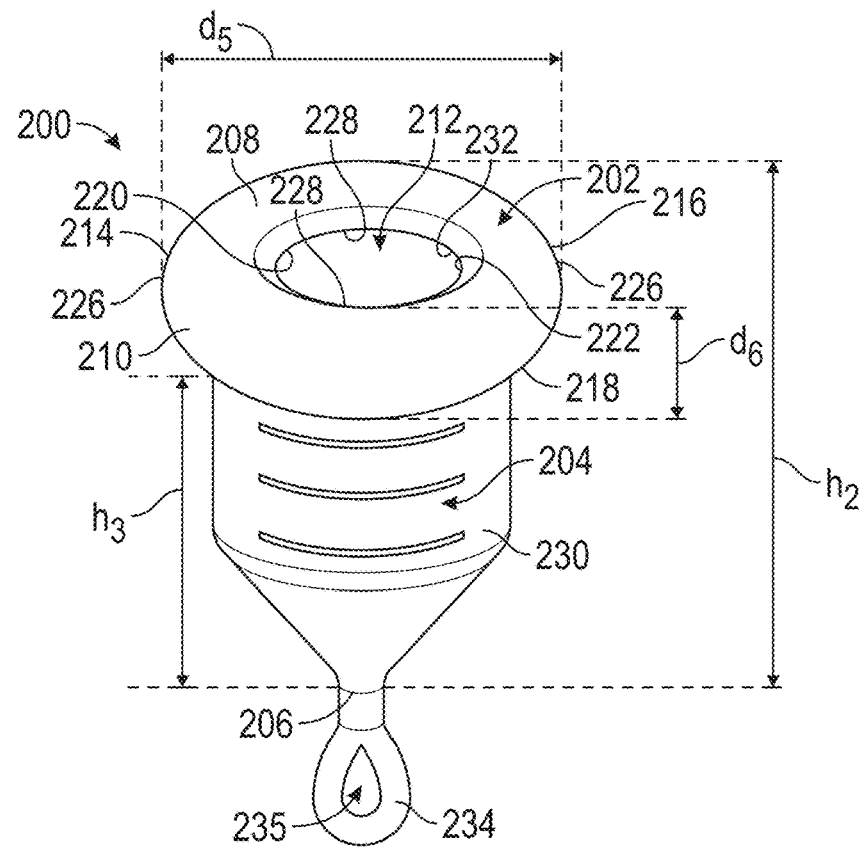
FIG. 11: Illustration of the second non-limiting example embodiment of the combined pessary and menstrual cup with a stem.

Referring to FIG. 11, it is advantageous for the stem 234 to be circular shaped with a hole 235 therethrough so the user can easily grasp the stem 234 by placing a finger through the hole 235 of the stem 234. The stem 234 can be located at any point on the cup portion 204 or the base ring 210. However, the stem 234 being located on the cup bottom point 206 allows the stem 234 to be most easily reached when in position within the body. Alternatively or in addition, the stem 234 may be formed from a piece of silicone extending between the cup bottom point 206 and the base ring 210. In this manner, the user can easily break the seal formed between the combined pessary and menstrual cup 200 and vaginal canal by simply grasping the stem 234 and pulling on it. However, the stem 234 can also be located elsewhere on the combined pessary and menstrual cup 200, such as anywhere on the base ring 210 or even on the exterior surface 230 of the cup portion 204.

As noted above, the combined pessary and menstrual cup 100, 200 can be made from a medical grade silicone. The combined pessary and menstrual cup 100, 200 can be fabricated through any method for manufacturing silicone parts, including, but not limited to, injection molding. Injection molding allows a manufacturer to produce large quantities in a short period of time. Injection molding offers a simple and fast process, especially when using silicone. Furthermore, injection molding is beneficial because it easily allows a manufacturer to have multiple different molds to allow for a wide range of sizes and shapes of the combined pessary and menstrual cups 100, 200 to be readily available for manufacturing. However, other methods of producing the combined pessary and menstrual cups 100, 200 are possible and encompassed within the scope of the present disclosure. Non-limiting examples of such other methods include blow molding, extrusion molding, compression molding, transfer molding, flash molding, melt molding, or rotational molding.

Figure 12:
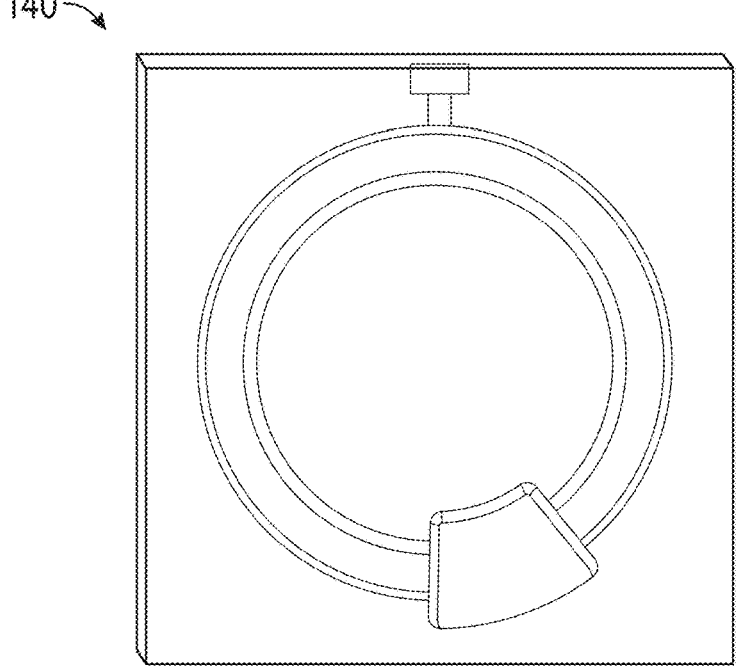
FIG. 12: Illustration of a non-limiting example embodiment of a mold for the first non-limiting example embodiment of the combined pessary and menstrual cup.
Figure 13:
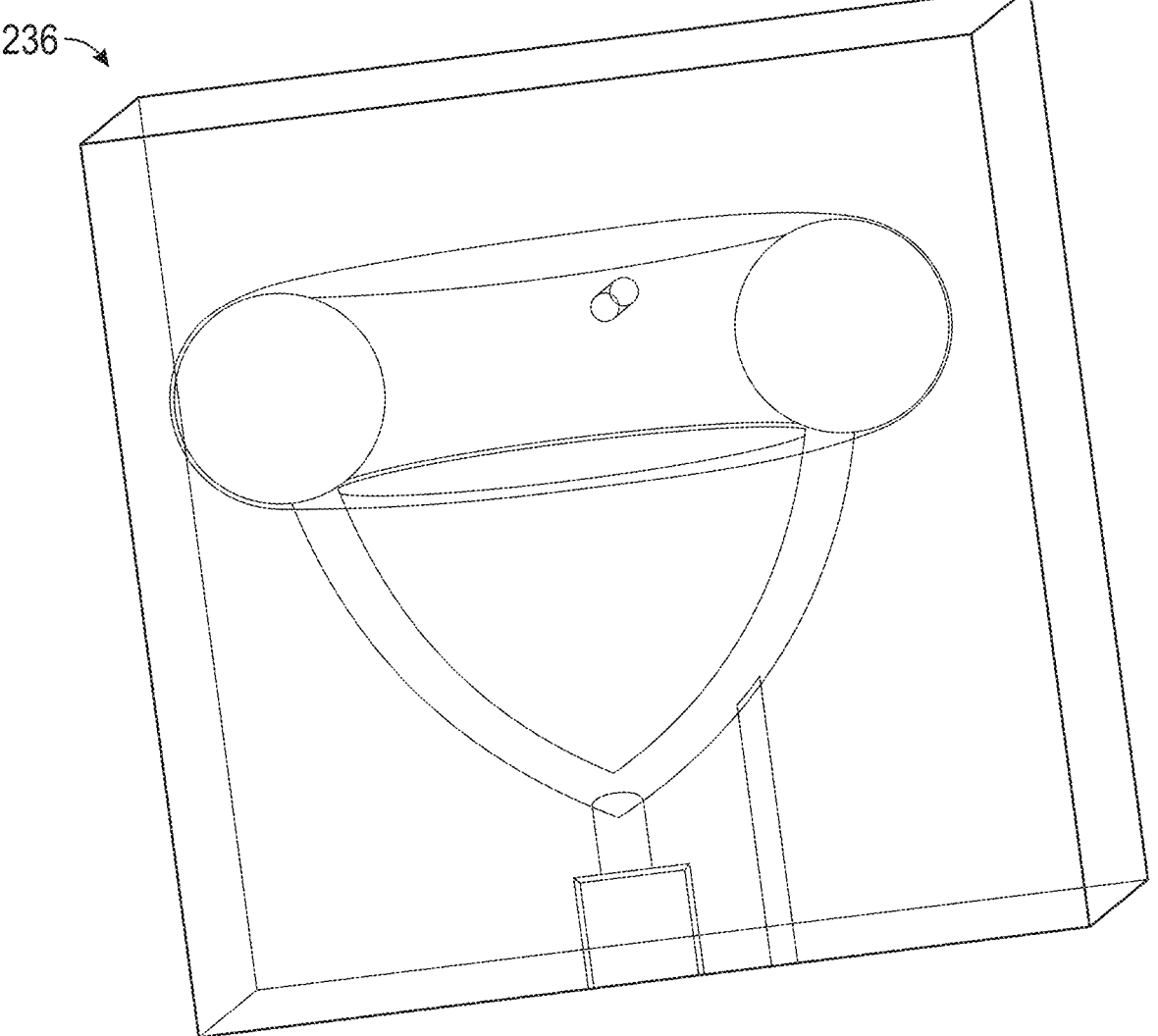
FIG. 13: Illustration of a non-limiting example embodiment of a mold for the second non-limiting example embodiment of the combined pessary and menstrual cup.

Each of FIGS. 12 and 13 illustrates non-limiting example molds 140, 236 for fabricating the first and second combined pessary and menstrual cups 100, 200 respectively. Referring now to FIGS. 12-13, in one non-limiting example method to manufacture a combined pessary and menstrual cup 100, 200 through injection molding, the first step is to make a mold 140, 236. Next, silicon is mixed with resin and then poured into the mold 140, 236. Then, the silicone is left to cure for a suitable time, usually at least 24 hours. Finally, the combined pessary and menstrual cup 100, 200 is removed from the mold 140, 236. However, other injection molding processes are possible and encompassed within the scope of the present disclosure.

Silicone is also useful for reasons unrelated to the manufacturing method used to produce the combined pessary and menstrual cup 100, 200. Using silicone is beneficial because it is durable, does not release toxins, is antibacterial/hypoallergenic, is soft and flexible, is resistant to temperature change, has a Young's Modulus of 130-180 GPA, and has a Poisson's Ratio of 0.48-0.495. These properties of silicone provide a product that is comfortable, easy to use, easy to clean, and safe to use in the body. Although silicone is the preferred material for using to make the combined pessary and menstrual cups 100, 200, any other material commonly used in the art of pessaries, menstrual cups, and menstrual discs can be used in the manufacture of combined pessary and menstrual cups 100, 200.

To use the combined pessary and menstrual cup 100, 200, a person can insert the combined pessary and menstrual cup from their desired comfortable position, such as standing with one foot elevated on a chair or lying down on their back with their knees bent and legs spread apart. A lubricant can be applied to the combined pessary and menstrual cup 100, 200 to more easily insert and position the combined pessary and menstrual cup 100, 200. The lubricant may be, for example, a water-based lubricant, as some oil-based lubricants may cause damage to the material of the combined pessary and menstrual cup 100, 200. However, the use of oil-based lubricants is nonetheless possible and encompassed within the scope of the present disclosure. For insertion, the combined pessary and menstrual cup 100, 200 can be held between a thumb and a forefinger, ensuring a firm grip is in place. Using another hand, the labia can be carefully separated to access the vaginal opening. Slowly and steadily, the combined pessary and menstrual cup 100, 200 can be inserted into the vagina, and should be aimed towards the small of the user's back. A user can adjust the position of the combined pessary and menstrual cup 100, 200 with the user's index finger to push the combined pessary and menstrual cup 100, 200 further inside until the combined pessary and menstrual cup 100, 200 is comfortably in place. Once the combined pessary and menstrual cup 100, 200 is inserted, its position may need to be adjusted to ensure that is properly placed. This can be done by gently pushing or rotating the combined pessary and menstrual cup 100, 200 with a finger. The combined pessary and menstrual cup should rest comfortably against the vaginal walls without causing any discomfort. After positioning the combined pessary and menstrual cup 100, 200, there should be no pain, irritation, or discomfort. When inserting the first example embodiment of the combined pessary and menstrual cup 100, the knob 112 should be positioned towards the organ against which pressure is desired, such as the urethra.

While in position, the combined pessary and menstrual cup 100, 200 will both (i) treat urinary incontinence or a pelvic organ prolapse and (ii) collect and retain menstrual blood and mucous. Once it is desired to remove the combined pessary and menstrual cup 100, 200, the seal that forms between the base ring 110, 210 and the vaginal canal can be broken before pulling the combined pessary and menstrual cup 100, 200 toward the vaginal opening. The seal can be broken by flexing the combined pessary and menstrual cup as depicted, for example, in FIGS. 3-4. If the combined pessary and menstrual cup includes a stem 138, 234, then a pulling force can be applied to the stem 138, 234 in order to break the seal and remove the combined pessary and menstrual cup 100, 200. Advantageously, the combined pessary and menstrual cup can be removed easily by a user without the need for a medical professional. Furthermore, once removed, the combined pessary and menstrual cup 100, 200 can be cleaned or disinfected with any cleaning agent suitable for cleaning or disinfecting silicone or other medical product materials.

Certain embodiments of the devices and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the devices and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A combined pessary and menstrual cup comprising:
a ring portion comprising a knob extending radially outwardly from a base ring along a portion of a circumference of the base ring; and
a cup portion extending from the base ring to a cup bottom point and defining an internal volume configured to retain a volume of liquid, wherein the base ring defines an opening to the internal volume.

2. The combined pessary and menstrual cup of claim 1, wherein the internal volume is in a range of from about 8 mL to about 79 mL.

3. The combined pessary and menstrual cup of claim 1, wherein the knob takes up from about one-eighth to about one-fourth of the circumference of the base ring.

4. The combined pessary and menstrual cup of claim 1, wherein the knob has a thickness diameter measured from a top surface of the knob to a bottom surface of the knob, the base ring has a thickness diameter measured from a top surface of the base ring to a bottom surface of the base ring, and the thickness diameter of the knob is larger than the thickness diameter of the base ring.

5. The combined pessary and menstrual cup of claim 4, wherein the thickness diameter of the knob is from about 10% larger to about 300% larger than the thickness diameter of the base ring.

6. The combined pessary and menstrual cup of claim 4, wherein the thickness diameter of the knob is about two times larger than the thickness diameter of the base ring.

7. The combined pessary and menstrual cup of claim 1, wherein the knob is trapezoidal in shape.

8. The combined pessary and menstrual cup of claim 1, wherein the knob is solid.

9. The combined pessary and menstrual cup of claim 1, further comprising a support member spanning the opening.

10. The combined pessary and menstrual cup of claim 9, wherein the support member comprises at least one hole therethrough.

11. The combined pessary and menstrual cup of claim 1, wherein the cup portion extends from an exterior surface of the base ring, and wherein the cup bottom point is concentric with the base ring.

12. The combined pessary and menstrual cup of claim 1, wherein the cup portion extends from an interior surface of the base ring, and wherein the cup bottom point is concentric with the base ring.

13. The combined pessary and menstrual cup of claim 1, wherein the cup portion extends from a bottom surface of the base ring, and wherein the cup bottom point is concentric with the base ring.

14. The combined pessary and menstrual cup of claim 1, further comprising a stem protruding from the cup portion.

15. The combined pessary and menstrual cup of claim 14, wherein the stem extends from the cup bottom portion to the knob.

16. The combined pessary and menstrual cup of claim 14, wherein the stem protrudes from the knob.

17. A combined pessary and menstrual cup comprising:
a ring portion comprising a base ring; and
a cup portion extending from an interior surface of the base ring to a cup bottom point and defining an internal volume configured to retain a volume of liquid, wherein the base ring defines an opening to the internal volume;
wherein the base ring has a thickness diameter measured from a top surface of the base ring to a bottom surface of the base ring, the cup portion has a cup height measured from a plane defined by a bottom surface of the base ring to a parallel plane defined by the cup bottom point, and a ratio of the thickness diameter to the cup height is from about 0.60:1 to about 3:1; and
wherein a loop diameter from a first side of the base ring to a second side of the base ring is from about 51 mm to about 95 mm.

18. The combined pessary and menstrual cup of claim 17, wherein the thickness diameter is greater than 75% of the cup height.

19. The combined pessary and menstrual cup of claim 17, wherein the combined pessary and menstrual cup has a height measured from a plane defined by a top surface of the base ring to a parallel plane defined by the cup bottom point, and the thickness diameter is at least half of the height.

20. The combined pessary and menstrual cup of claim 17, further comprising a stem extending from the cup bottom point.

* * * * *